United States Patent
Zhang et al.

(10) Patent No.: US 9,002,443 B2
(45) Date of Patent: Apr. 7, 2015

(54) SYSTEM AND METHOD FOR AVOIDING UNDERSENSING OF VENTRICULAR FIBRILLATION

(71) Applicant: Medtronic, Inc., Minneapolis, MN (US)

(72) Inventors: Xusheng Zhang, Shoreview, MN (US);
Mark L. Brown, North Oaks, MN (US);
Paul J. DeGroot, Shoreview, MN (US);
Saul E. Greenhut, Aurora, CO (US);
Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 6 days.

(21) Appl. No.: 13/833,171

(22) Filed: Mar. 15, 2013

(65) Prior Publication Data
US 2014/0276160 A1    Sep. 18, 2014

(51) Int. Cl.
| | | |
|---|---|---|
| *A61B 5/046* | (2006.01) | |
| *A61B 5/0464* | (2006.01) | |
| *A61N 1/39* | (2006.01) | |
| *A61B 5/00* | (2006.01) | |
| *A61B 5/0452* | (2006.01) | |
| *A61N 1/362* | (2006.01) | |

(52) U.S. Cl.
CPC ............... *A61B 5/0464* (2013.01); *A61B 5/046* (2013.01); *A61N 1/395* (2013.01); *A61B 5/7264* (2013.01); *A61N 1/3956* (2013.01); *A61B 5/04525* (2013.01); *A61N 1/3621* (2013.01); *A61B 5/6869* (2013.01)

(58) Field of Classification Search
CPC .... A61N 1/37; A61N 1/372; A61N 2001/083
USPC .................. 607/8, 28; 324/649; 600/518
See application file for complete search history.

(56) References Cited

U.S. PATENT DOCUMENTS

| | | | |
|---|---|---|---|
| 5,632,766 A * | 5/1997 | Hsu et al. .................... 607/5 |
| 6,393,316 B1 | 5/2002 | Gillberg | |
| 6,526,313 B2 | 2/2003 | Sweeney | |
| 7,076,289 B2 | 7/2006 | Sarkar | |
| 7,474,916 B2 | 1/2009 | Gutierrez | |
| 7,742,812 B2 | 6/2010 | Ghanem | |
| 7,904,153 B2 | 3/2011 | Greenhut | |
| 7,930,020 B2 | 4/2011 | Zhang | |
| 7,991,459 B2 | 8/2011 | Palreddy | |

(Continued)

OTHER PUBLICATIONS

(PCT/US2014/020998) PCT Notification of Transmittal of the International Search Report and the Written Opinion of the International Searching Authority, Sep. 25, 2014.

*Primary Examiner* — Carl H Layno
*Assistant Examiner* — Erin Piateski
(74) *Attorney, Agent, or Firm* — Michael C. Soldner (57) ABSTRACT

A medical device and associated method for detecting and treating tachyarrhythmias acquires a cardiac signal using electrodes coupled to a sensing module. Cardiac events are sensed from the cardiac signal and a processing module computes a first morphology metric for each sensed cardiac event occurring during a time segment of the cardiac signal. The first morphology metrics corresponding to an event originating in a ventricular chamber are counted. The first processing module computes a second morphology metric for the time segment of the cardiac signal in response to the count of the first morphology metrics meeting a threshold number of events. The time segment is classified as a shockable segment in response to the second morphology metric meeting a detection criterion.

11 Claims, 5 Drawing Sheets

(56) References Cited

U.S. PATENT DOCUMENTS

| | | |
|---|---|---|
| 8,145,301 B2 | 3/2012 | Kim |
| 8,160,684 B2 | 4/2012 | Ghanem |
| 8,315,699 B2 | 11/2012 | Stadler |
| 2004/0249418 A1* | 12/2004 | Mills et al. .................... 607/5 |
| 2006/0025825 A1* | 2/2006 | Bowers .......................... 607/5 |
| 2007/0232944 A1* | 10/2007 | Ghanem et al. ............. 600/509 |
| 2007/0232948 A1 | 10/2007 | Stadler et al. |
| 2007/0239046 A1* | 10/2007 | Ghanem et al. ............. 600/509 |
| 2008/0269624 A1* | 10/2008 | Zhang et al. ................ 600/508 |
| 2008/0269813 A1* | 10/2008 | Greenhut et al. ................ 607/5 |
| 2009/0105778 A1* | 4/2009 | Lee et al. ........................ 607/17 |
| 2011/0021934 A1* | 1/2011 | Kim et al. .................... 600/518 |
| 2011/0106218 A1* | 5/2011 | Stancer et al. ................. 607/63 |
| 2011/0270109 A1 | 11/2011 | Zhang et al. |
| 2011/0270335 A1* | 11/2011 | Stadler et al. .................... 607/5 |
| 2011/0270341 A1* | 11/2011 | Ruben et al. ..................... 607/9 |
| 2012/0004566 A1* | 1/2012 | Zhang et al. ................ 600/515 |
| 2012/0053477 A1 | 3/2012 | Zhang et al. |
| 2012/0323290 A1* | 12/2012 | Warren et al. .................... 607/7 |
| 2013/0030481 A1 | 1/2013 | Ghosh |

\* cited by examiner

FIG. 6

SYSTEM AND METHOD FOR AVOIDING UNDERSENSING OF VENTRICULAR FIBRILLATION

TECHNICAL FIELD

The disclosure relates generally to implantable medical devices and, in particular, to an apparatus and method for avoiding ventricular fibrillation undersensing.

BACKGROUND

Implantable medical devices are available for treating cardiac arrhythmias by delivering anti-tachycardia pacing therapies and electrical shock therapies for cardioverting or defibrillating the heart. Such a device, commonly known as an implantable cardioverter defibrillator or "ICD", conventionally senses a patient's heart rate and classifies the rate according to a number of heart rate zones in order to detect episodes of tachycardia or fibrillation. Typically a number of predefined rate zones are defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into defined detection interval ranges are counted to provide a count of VT or VF intervals. A programmable number of intervals to detect (NID) defines the number of tachycardia intervals occurring consecutively or out of a given number of preceding event intervals that are required to detect VT or VF.

Tachyarrhythmia detection may begin with detecting a fast ventricular rate, referred to as a rate- or interval-based detection. Once VT or VF is detected based on rate, the morphology of the sensed depolarization signals may be used in discriminating heart rhythms to improve the sensitivity and specificity of tachyarrhythmia detection methods. Before a therapy decision is made, tachyarrhythmia detection may further require discrimination between SVT and VT using cardiac signal waveform morphology analysis, particularly when a fast 1:1 atrial to ventricular rate is being sensed. However, the sensitivity of tachyarrhythmia detection algorithms relying on rate-based detection as a primary detection method are limited to the reliability of sense amplifiers in accurately sensing P-waves and R-waves and by the selection of the rate zone thresholds for VT and VF detection. Rate-based arrhythmia detection schemes that rely primarily on P-wave and R-wave sensing are subject to limitations due to oversensing and undersensing of depolarization signals, which can result in either overestimating or underestimating the actual heart rate. Inadequately programmed rate zone thresholds can also cause over- or under-detection of tachyarrhythmias that might be responsive to ICD therapy. Undersensing of VF, e.g. due to undersensing of ventricular signals or other factors, can occur. The highest priority goal of an ICD is generally achieving high sensitivity to VF detection, since sustained VF is a life-threatening condition and requires prompt detection and treatment.

DETAILED DESCRIPTION

An IMD, or other device, according to the present disclosure includes tachycardia detection modules operating in parallel. One module operates to detect and discriminate all tachyarrhythmias, i.e. SVT, VT and VF, using a combination of RR interval measurements and morphology analysis. The other module operates to detect VF only using only morphology-based criteria, i.e. no heart rate determination or RR interval counts, such that the VF detection module is not subject to oversensing or undersensing of R-waves. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

An SVT/VT/VF detection module and a VF-only detection module operating simultaneously provide parallel paths to VF detection. The VF detection module, which does not rely on RR interval counting or heart rate determination, reduces the likelihood of VF undersensing due to R-wave oversensing or undersensing. During R-wave undersensing, RR interval counts may not reach the required VF NID. During R-wave oversensing, noise may be present masking a true ventricular rate. VF undersensing may occur during either conditions or detection of VF may be delayed.

When relying on RR interval counts or other rate-based analysis as a criterion for detecting VF, additional analysis of the cardiac signal may be utilized to identify potential noise and/or patterns of undersensing in an attempt to correct RR interval counts. However, the parallel path approach to VF detection disclosed herein that does not rely on RR interval counts enables rapid VF detection without waiting for VF NID criteria (or other heart rate-based criteria) to be reached and without requiring additional analysis for noise and undersensing, which could delay VF detection. The detection of VF is the top priority of the IMD detection operations to enable rapid treatment of malignant VF episodes.

Figure 1:
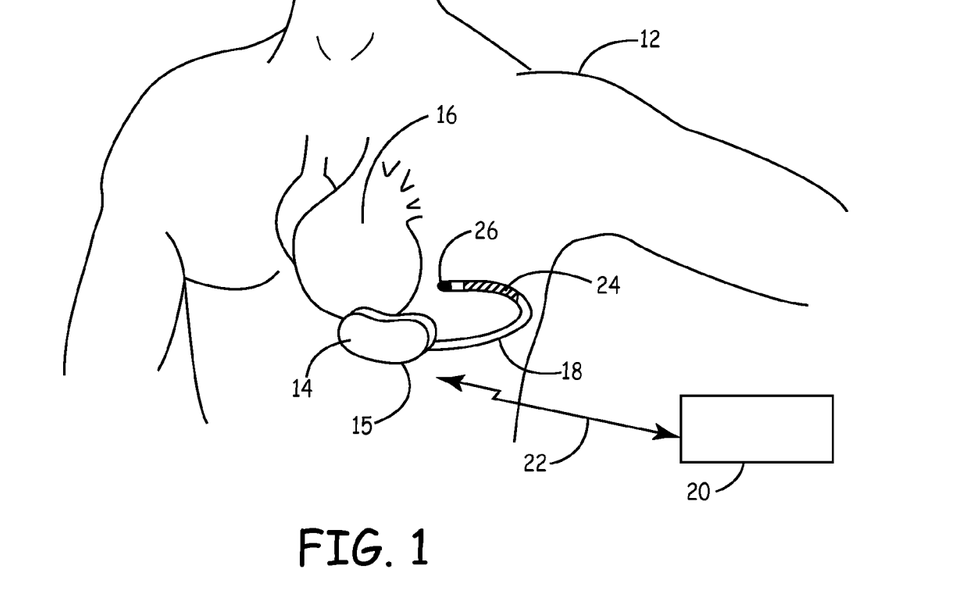
FIG. 1 and FIG. 2 are schematic diagrams of an implantable medical device (IMD) in which methods described herein may be usefully practiced.
Figure 2:
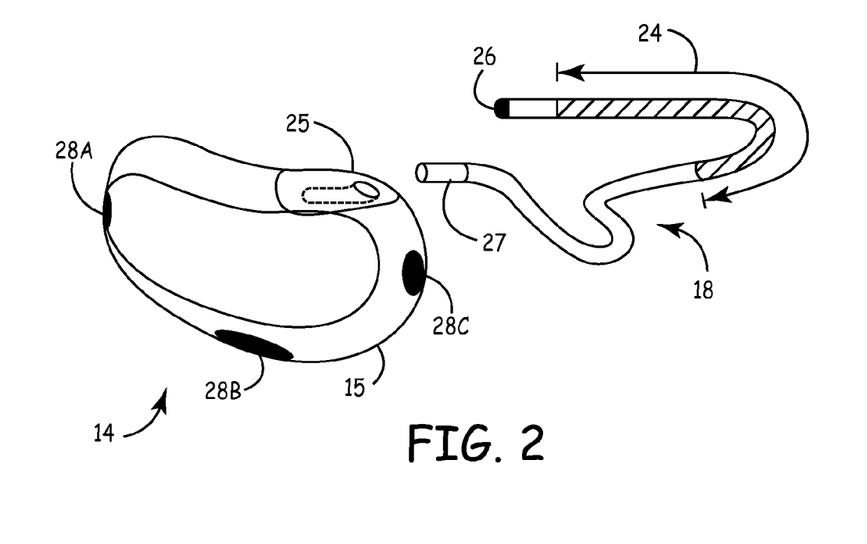

FIG. 1 and FIG. 2 are schematic diagrams of an IMD in which methods described herein may be usefully practiced. As illustrated in FIG. 1, IMD 14 according to one embodiment is subcutaneously implanted outside the ribcage of a patient 12, anterior to the cardiac notch. IMD 14 includes a housing 15 to enclose electronic circuitry of the device 14.

In the example shown, sensing and cardioversion/defibrillation therapy delivery lead 18 in electrical communication with IMD 14 is tunneled subcutaneously into a location adjacent to a portion of a latissimus dorsi muscle of patient 12. Specifically, lead 18 is tunneled subcutaneously from a median implant pocket of IMD 14 laterally and posteriorly to the patient's back to a location opposite the heart such that the heart 16 is disposed between IMD 14 and a distal electrode coil 24 and a distal sensing electrode 26 of lead 18. Other lead configurations and implant positions may be used.

Subcutaneous lead 18 includes a distal defibrillation coil electrode 24, a distal sensing electrode 26, an insulated flexible lead body and a proximal connector pin 27 (shown in FIG. 2) for connection to subcutaneous device 14 via a connector 25. In addition, one or more electrodes 28A, 28B, 28C, collectively 28, (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array. It is understood that while IMD 14 is shown with electrodes 28 positioned on housing 15, electrodes 28 may be alternatively positioned along one or more separate leads connected to device 14 via connector 25. The lead and electrode configuration shown in FIG. 1 is merely illustrative of one arrangement of electrodes that can be used for sensing subcutaneous ECG signals and delivering cardioversion/defibrillation shocks. Numerous configurations may be contemplated that include one or more housing-based electrodes and/or one or more lead-based electrodes for enabling sensing of an ECG signal along one or more sensing vectors using extra-vascular, extra-cardiac electrodes implanted beneath the skin, muscle or other tissue layer within a patient's body.

The tachyarrhythmia detection techniques disclosed herein are useful in an IMD system utilizing subcutaneous ECG sensing electrodes. A subcutaneous IMD system is less invasive and more easily implanted than a system including transvenous or epicardial leads. However, the ECG signal amplitude is small, e.g. about one-tenth of the amplitude of cardiac electrogram (EGM) signals sensed using transvenous leads carrying intracardiac electrodes or epicardial leads and electrodes. R-wave undersensing, and consequently VF undersensing, may be more likely to occur in an IMD system relying on subcutaneous ECG sensing than intracardiac EGM sensing.

The parallel path approach disclosed herein that enables VF detection with less dependence on accurate RR interval measurements is therefore advantageous in subcutaneous IMD systems, such as the system illustrated in FIG. 1. However, the techniques disclosed herein may be implemented in any ICD system, which may include any combination of intracardiac, epicardial, subcutaneous, lead-based and/or housing based electrodes. Accordingly, the description of VF detection methods presented herein refers primarily to analysis of subcutaneous ECG signals for the sake of illustration, but it is contemplated that in other embodiments EGM signals or a combination of ECG (subcutaneous or surface) and EGM signals might be used for tachyarrhythmia detection and discrimination by a medical device configured to detect tachyarrhythmia and delivery tachyarrhythmia therapies.

Further referring to FIG. 1, a programmer 20 is shown in telemetric communication with IMD 14 by an RF communication link 22. Communication link 22 may be any appropriate RF link such as Bluetooth, WiFi, or Medical Implant Communication Service (MICS). Programmer 20 is used to retrieve data from IMD 14 and to program operating parameters and programs in IMD 14 for controlling IMD 14 functions. For example, programmer 20 may be used to program tachyarrhythmia detection parameters, such as VT and VF interval zones, VT and VF NID, and detection thresholds relating to morphology analysis of the cardiac signals.

IMD 14 and associated lead 18 are referred to as a "subcutaneous IMD system" because lead 18 is positioned in an extravascular location, subcutaneously. It is understood that while IMD 14 and lead 18 may be positioned between the skin and muscle layer of the patient, IMD 14 and any associated leads could be positioned in any extravascular location of the patient, such as below the muscle layer or within the thoracic cavity, for example.

Figure 3:
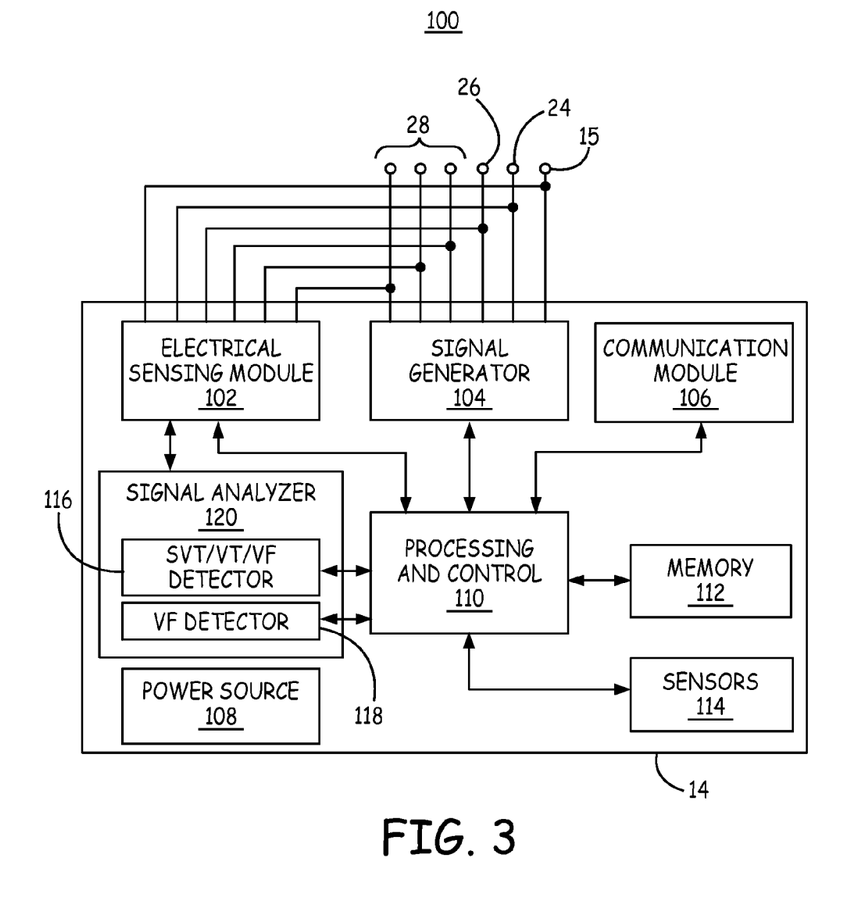
FIG. 3 is a functional block diagram of electronic circuitry that is included in one embodiment of the IMD shown in FIG. 1 for practicing the methods described herein.

FIG. 3 is a functional block diagram 100 of electronic circuitry that is included in one embodiment of IMD 14 shown in FIG. 1 for practicing the methods described herein.

The IMD 14 includes electrical sensing module 102, signal generator module 104, communication module 106, processing and control module 110 and associated memory 112, and cardiac signal analyzer 120. A power source 108 provides power to each of the modules 102, 104, 106, 110, 112, 114 and 120. Power source 108 may include one or more energy storage devices, such as one or more primary or rechargeable batteries.

Modules included in IMD 14 represent functionality that may be included in IMD 14 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, integrated circuits, memory devices, etc. Memory may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Furthermore, memory 112 may include non-transitory computer readable media storing instructions that, when executed by one or more processing circuits, cause the modules to perform various functions attributed to the modules herein. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, tachyarrhythmia detection operations performed by cardiac signal analyzer 120 may be implemented in a processing and control module 110 executing instructions stored in memory 112.

Processing and control module 110 communicates with signal generator module 104, cardiac signal analyzer 120 and electrical sensing module 102 for sensing cardiac electrical activity, detecting cardiac rhythms, and generating cardiac therapies in response to sensed signals. Signal generator module 104 and electrical sensing module 102 are electrically coupled to subcutaneous SEA electrodes 28 incorporated along but electrically insulated from IMD housing 15, lead-based electrodes 24 and 26 and housing 15, at least a portion of which also serves as a common or ground electrode and is therefore also referred to herein as "housing electrode" 15.

Electrical sensing module 102 is configured to monitor signals from available electrodes 26 and 28 (or other sensing electrodes) in order to monitor electrical activity of a patient's heart. Electrical sensing module 102 may selectively monitor one or more sensing vector selected from available electrodes. Sensing module 102 may include switching circuitry for selecting which of electrodes 24, 26, 28 and housing electrode 15 are coupled to sense amplifiers included in sensing module 102. Switching circuitry may include a switch array, switch matrix, multiplexer, or any other type of switching device suitable to selectively couple sense amplifiers to selected electrodes. Sensing vectors will typically be selected from SEA electrodes 28 in combination with lead-based sensing electrode 26 although it is recognized that in some embodiments sensing vectors may be selected that utilize coil electrode 24 and/or housing electrode 15.

Sensing module 102 provides sense event signals corresponding to the timing of sensing R-waves (and P-waves in some embodiments) and digitized ECG signals to cardiac signal analyzer 120. Cardiac signal analyzer 120 includes an SVT/VT/VF detector 116 and a VF detector 118 that operate in parallel to detect tachyarrhythmia episodes as described in detail below. Some aspects of sensing and processing subcutaneous ECG signals are generally disclosed in commonly-assigned U.S. Pat. No. 7,904,153 (Greenhut, et al.), hereby incorporated herein by reference in its entirety. Operations performed by SVT/VT/VF detector 116 for detecting and discriminating tachyarrhythmias may include techniques generally disclosed in U.S. Pat. No. 7,742,812 (Ghanem, et. al) and U.S. Pat. No. 8,160,684 (Ghanem, et. al), both of which patents are incorporated herein by reference in their entirety.

Electrical sensing module 102 may include signal conditioning circuits, e.g., amplification and filtering circuits that amplify and filter cardiac electrical signals received from electrodes 26 and 28. Electrical sensing module 102 includes analog-to-digital (A/D) conversion circuits that digitize the conditioned cardiac electrical signals. The digitized data generated by the A/D circuits included in electrical sensing module 102 may be referred to as "raw data." In some examples, the A/D circuits may include an 8-bit A/D converter that samples conditioned cardiac electrical signals at approximately 256 Hz. Sensing module 102 generates R-wave sense signals upon sensing an R-wave from the ECG signal, for example based on an auto-adjusted threshold crossing of the ECG signal. The timing of an R-wave sense signal is used by SVT/VT/VF detector 116 to measure R-R intervals for counting RR intervals in different detection zones or determining a heart rate or other rate-based measurements for detecting tachyarrhythmia. The timing of R-wave sense signals are used by VF detector 118 for setting beat morphology analysis windows in some embodiments.

In some embodiments, sensing module 102 may include multiple sensing channels having different sensing bandwidths. The different sensing channels may be coupled to the same or different sensing electrode vectors selected from SEA electrodes 28 and lead-based sensing electrode 26. In one embodiment, sensing module 102 includes a wide-band channel having a bandwidth of approximately 2.5 Hz to 95 Hz and a narrow-band channel having a sensing bandwidth between 2.5 Hz and 23 Hz. Both channels may be used for providing digitized raw ECG signals to cardiac signal analyzer 120 for performing morphology analysis. Alternatively, the wide band channel or the narrow band channel may be used alone or in combination for performing the morphology analysis. In some embodiments, a third channel having a third pass band different than the morphology signal channels is used for sensing R-wave signals. For example, an R-wave sensing channel may have a pass band intermediate the narrow band and wide band sensing channels, e.g., approximately 10 Hz to 35 Hz.

Cardiac signal analyzer 120 receives R-wave sense signals and raw ECG signals from electrical sensing module 102 and detects cardiac tachyarrhythmias based on the R-wave sense signals and raw ECG signals and processing thereof. As further described below, SVT/VT/VF detector uses RR interval counters or a heart rate measurement to detect a tachyarrhythmia based on the ventricular rate and then initiates a morphology analysis to discriminate between SVT, VT, VF and noise.

VF detector uses analysis of individual cardiac cycle signal morphology, i.e. "beat morphology" to detect beats originating in the ventricles, also referred to herein as "ventricular beats" and then initiates an extended morphology analysis over an interval of time to detect VF.

When SVT/VT/VF detector 116 detects a tachyarrhythmia, SVT/VT/VF detector 116 provides a detection signal to processing and control module 110 indicating the current detection state as SVT, VT or VF. When VF detector 118 detects a tachyarrhythmia, a VF detection signal is provided to processing and control module 110. The VF detection signal from VF detector 118 is given the highest priority by processing and control module 110 in controlling a therapy response. In other words, a VF detection signal from VF detector 118 will override any non-VF detection signal currently being received from SVT/VT/VF detector 116. Processing and control module 110 will respond to a VF detection signal from VF detector 118 by immediately controlling signal generator 104 to deliver a defibrillation shock pulse, for example using coil electrode 24 and housing electrode 15.

If processing and control module 110 is not receiving a VF detection signal from VF detector 118, processing and control module 110 responds to any SVT, VT or VF detection signal being received from SVT/VT/VF detector 116. For example, if a fast ventricular rate has been detected, but the current detection state signal from SVT/VT/VF detector 116 is SVT and no VF detection signal is output from VF detector 118, control module 110 will withhold a cardioversion/defibrillation therapy. If the SVT/VT/VF detector 116 is providing a VT detection signal, control module 110 will respond by controlling signal generator 104 to deliver a programmed therapy, such as anti-tachycardia pacing or cardioversion shock therapy, as long as no VF detection signal is being received from VF detector 118. In some cases, SVT/VT/VF detector 116 may be providing a VF detection signal to control 110 when VF detector 118 is not. Control 110 may respond to a VF detection signal from SVT/VT/VF detector 116 by controlling signal generator 104 to deliver a defibrillation shock even when VF detector 118 is not outputting a VF detection signal.

It should be noted that implemented tachyarrhythmia detection algorithms may utilize not only ECG signal analysis methods but may also utilize supplemental sensors 114, such as tissue color, tissue oxygenation, respiration, patient activity, heart sounds, and the like, for contributing to a decision by processing and control module 110 to apply or withhold a defibrillation therapy. In particular, in one embodiment, when processing and control module 110 receives a VF detection signal from VF detector 118, processing and control module 110 may control signal generator 104 to deliver a defibrillation therapy only when an activity sensor signal is indicative of low activity. Alternatively, VF detector 118 may receive a signal from an activity sensor included in sensors 114 and generate a VF detection signal only in response to a low activity signal in combination with morphology-based VF detection criteria being satisfied.

In response to a VT or VF detection as described above, processing and control module 110 may control signal generator module 104 to deliver a shock therapy using coil electrode 24 and housing electrode 15 according to one or more therapy programs, which may be stored in memory 112. For example, processing and control module 110 may control signal generator module 104 to deliver a shock pulse at a first energy level and increase the energy level upon redetection of a VT or VF rhythm. Shock pulse generation and control is further described in the above incorporated '153 Greenhut patent. In some embodiments, an IMD configured with parallel SVT/VT/VF detector 116 and VF detector 118 may be capable of delivering other tachyarrhythmia therapies, such as anti-tachycardia pacing (ATP) in response to a VT detection signal from SVT/VT/VF detector 116 and no VF detection signal from VF detector 118.

Communication module 106 includes any suitable hardware, firmware, software or any combination thereof for communicating with another device, such as an external programmer 20 and/or a patient monitor. Under the control of processing module 110, communication module 106 may receive downlink telemetry from and send uplink telemetry to programmer 20 and/or a patient monitor with the aid of an antenna (not shown) in IMD 14.

Processing and control module 102 may generate marker channel data based on analysis of the raw data. The marker channel data may include data that indicates the occurrence and timing of sensing, diagnosis, and therapy events associated with IMD 14. Processing and control module 110 may store the generated marker channel data in memory 112. Although not illustrated, in some examples, marker channel data may include information regarding the performance or integrity of IMD 14, including power source 108 and lead 18.

Processing and control module 110 may store raw data and marker channel data in memory 112. For example, processing and control module 110 may continuously store raw data from one or more electrode combinations in memory 112 as the raw data is received from electrical sensing module 102. In this manner, processing and control module 110 and cardiac signal analyzer 120 may use memory 112 as a buffer to store a predetermined amount of raw data. In some examples, processing and control module 110 may store raw data corresponding to a predetermined number of cardiac cycles, e.g., 12 cycles, or a desired number of predetermined time intervals of raw data. In other examples, processing and control module 110 may store a predetermined number of samples of raw data. Raw data buffered in memory 112 may be accessed by signal analyzer 120 for performing morphology analysis and detecting VT or VF.

Figure 4:
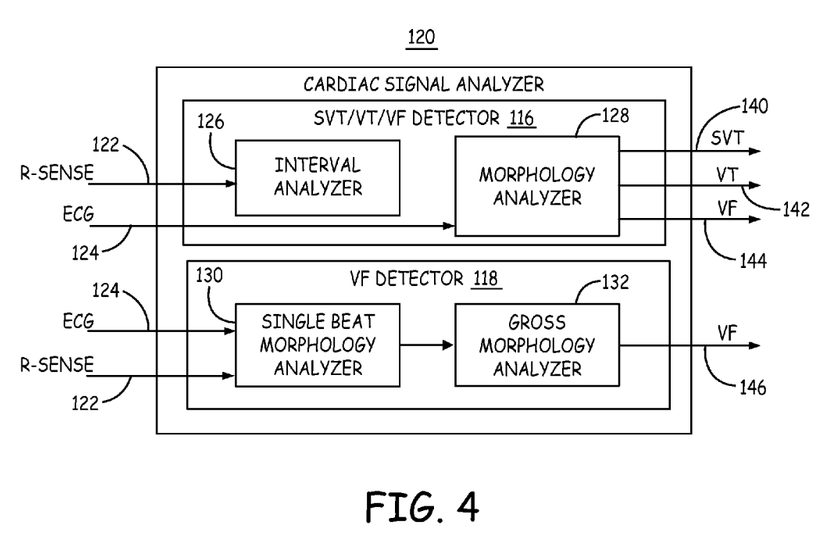
FIG. 4 is a functional block diagram of cardiac signal analyzer according to one embodiment.

FIG. 4 is a functional block diagram of cardiac signal analyzer 120 according to one embodiment. Cardiac signal analyzer 120 includes SVT/VT/VF detector 116 and VF detector 118, which each receive R-sense signals 122 from electrical sensing module 102 indicating the time an R-wave is sensed, e.g. by a sense amplifier having an auto-adjusting sensing threshold. Each of SVT/VT/VF detector 116 and VF detector 118 also receive raw digitized ECG signals 124 from sensing module 102. One difference, however, between SVT/VT/VF detector 116 and VF detector 118, is that SVT/VT/VF detector 116 does not analyze the raw ECG signal until an NID, or minimum heart rate, is reached based on measuring and counting or sorting RR intervals. The raw ECG signal may be buffered, for example in memory 112 or in a separate memory accessed by signal analyzer 120. SVT/VT/VF detector 116 only uses the ECG signal 124 for morphology analysis after a rate-based tachyarrhythmia detection criterion has been met. VF detector 116, however, uses the raw ECG signal 124 continuously to identify and count ventricular beats based on morphology. VF detector 116 may use the R-wave sense signal to identify beats for computing a morphology metric but, at least in some examples, never uses the R-wave sense signals for counting RR intervals or determining a heart rate as does SVT/VT/VF detector 116.

SVT/VT/VF detector 116 may operate to detect and discriminate tachycardia episodes using any desired algorithm that relies on RR interval measurements for primary detection criteria, e.g. NID or heart rate criteria. As such, SVT/VT/VF detector 116 includes an interval analyzer 126 receiving R-sense signal input 122. The interval analyzer 126 measures intervals between consecutively sensed R-waves, e.g. by determining an escape interval counter value upon receiving an R-wave sense signal. In some embodiments, the intervals are sorted by size and an nth longest interval is estimated as the heart rate. In other embodiments, the intervals are compared to the VT and VF detection zones, and VT and VF interval counters are increased accordingly. In some embodiments, a combined VT/VF counter may be used to count all intervals falling into either one of the VT or VF interval zones.

If an interval counter reaches a programmed NID or a heart rate measurement reaches a minimum heart rate, e.g. 180 bpm, a signal is provided to morphology analyzer 128 to begin morphology analysis to confirm and discriminate the detected tachyarrhythmia. In this way, the R-wave sense signals 122 are used to monitor ventricular rate continuously by interval analyzer 126, and the raw ECG signal 124 is used by morphology analyzer 128 intermittently whenever an NID or heart rate criterion has been satisfied based on measured RR intervals.

In some embodiments, interval analyzer 126 determines a heart rate from measured RR intervals for initial detection of a tachyarrhythmia before triggering morphology analyzer 128 to analyze the ECG signal 124. A minimum estimated heart rate of 180 bpm may be required before morphology analyzer 128 is enabled to perform morphology analysis. The heart rate may be estimated by interval analyzer 126 as the $n^{th}$ slowest RR interval of a selected number of most recent RR intervals that have been sorted by interval analyzer 126 from smallest to largest. In one embodiment, the heart rate is estimated as the $9^{th}$ slowest RR interval of the most recent 12 RR intervals. A heart rate may alternatively be estimated by interval analyzer 126 by other means, such as a mean RR interval, trimmed mean, or other methods.

In some cases, if the VF NID criterion or other heart rate criterion is satisfied, the SVT/VT/VF detector 116 may immediately generate a VF detection output signal 144. If a VT NID criterion (or other heart rate criterion) is satisfied, morphology analyzer 128 is invoked to perform morphology analysis to discriminate between a tachycardia originating in the atria, i.e. SVT, and VT. In other embodiments, morphology analyzer 128 performs morphology analysis to confirm a VF detection and to discriminate between VT/VF and SVT. Based on the outcome of the morphology analysis, one output signal SVT 140, VT 142, or VF 144 will go high indicating to processing and control module 110 the current detection state of SVT/VT/VF detector 116. When a fast rate is not being detected, all output signals SVT 140, VT 142 and VF 144 remain low, i.e. no detection signal is provided to control module 110.

Numerous morphology analysis techniques may be used for confirming a VT or VF detection and/or discriminating SVT from VT. Morphology analysis techniques may include computing a morphology match metric as a measure of the similarity between a cardiac cycle signal or R-wave to a normal sinus rhythm template. In one embodiment, wavelet analysis, e.g. as generally disclosed in U.S. Pat. No. 6,393, 316 (Gillberg et al.) may be performed to determine a morphology match metric for classifying ventricular beats and SVT beats and ultimately classifying the detected tachycardia as SVT or VT. In other embodiments, a gross morphology analysis may be performed that analyzes the cardiac signal across an entire n-second interval of time for determining morphology metrics that are compared to threshold criteria for detecting a ventricular rhythm. Examples of gross morphology analysis that may be implemented in morphology analyzer 128 or gross morphology analyzer 132 are generally disclosed in the above incorporated U.S. Pat. Nos. '812 and '684 (Ghanem, et al).

VF detector 118 operates in parallel and simultaneously to SVT/VT/VF detector 116. VF detector 118 includes a single beat morphology analyzer 130 and a gross morphology analyzer 132. Single beat morphology analyzer 130 receives the R-wave sense signals 122 and raw ECG signals 124 from sensing module 102. Unlike SVT/VT/VF detector 116, VF detector 118 does not use the R-wave sense signals to measure and count RR intervals. Single beat morphology analyzer 130 uses the sense signals 122 to set a morphology analysis window encompassing the sensed R-wave signal to classify ventricular beats, i.e. beats originating in the ventricles rather than the atria. Every R-wave sense signal is used to generate a single beat morphology analysis window over a predetermined n-second analysis time period or segment. In one embodiment, a three second analysis time segment is utilized.

For each R-wave sense signal that occurs during the n-second analysis segment, one or more beat morphology metrics are determined. In one embodiment, template matching may be performed, which may include aligning the unclassified beat, i.e. the signal waveform within the morphology analysis window, with a template of a known supraventricular beat, such as a normal sinus rhythm beat, and computing a metric of the similarity between the two beats. This computation may include performing wavelet analysis, computing a normalized area waveform difference, or other morphology comparison.

Additionally or alternatively, individual beat features may be extracted. Beat features that may be extracted during a morphology analysis window set in response to each R-wave sense signal may include any of a QRS width, R-wave width, R-wave polarity, and R-wave amplitude. Beat morphology metrics and beat features that do not require significant processing time to compute and compare to beat classification criteria may be implemented to provide rapid VF detection. The beat may be classified as a normal supraventricular beat, an abnormal ventricular beat, or an unidentified beat based on comparisons of a morphology match metric and/or one or more beat features to a classification threshold. Beats are classified as ventricular beats, for example, when a beat morphology metric has a weak correlation to an analogous metric of a normal supraventricular beat and thus has a relatively stronger correlation to an analogous metric of an abnormal, ventricular beat. Threshold ranges may be defined to classify a beat as supraventricular, ventricular or unidentified, which could be noise.

While R-wave sense signals may be used to perform beat-based morphology analysis by analyzer 130, it is contemplated that other methods may be used to identify individual "beats" or signals for morphological analysis within the n-second analysis segment. For example, a sample-by-sample template matching algorithm or searching for maximum peaks, slopes, zero-crossings or other techniques may be used to identify signals that are analyzed and classified as SVT beats, ventricular beats or unidentified signals.

If a minimum number of ventricular beats are identified, based on the single beat morphology analysis during the n-second analysis period, the gross morphology analyzer 132 is triggered to perform additional morphology analysis to detect VF. For example, if at least six ventricular beats are identified during a three-second analysis period, this frequency of ventricular beats during the three-second period suggests that ventricular fibrillation could be occurring. During the n-second analysis time period, R-wave undersensing could be occurring, preventing the interval analyzer 126 from reaching a VF NID or VF detection heart rate threshold. By detecting a threshold number of ventricular beats during a predetermined time period, however, VF can still be detected based on further morphology analysis of the ECG signal, even in the presence of R-wave undersensing.

The same n-second analysis period may be analyzed by gross morphology analyzer 132. Since some R-waves may be undersensed, RR intervals are not used. Instead, the evidence of ventricular beats provided by the single beat morphology analyzer 130 is supported by further analysis of morphology across the n-second analysis window to detect VF. Morphology metrics computed using the ECG signal sensed across the n-second time period are determined, and referred to as "gross" morphology metrics in contrast to single beat morphology metrics that are measured across a single cardiac cycle. The n-second window may start and end at any time point relative to an R-wave sense signal; the gross morphology metrics are therefore determined independent of identifying R-wave sense signals.

In one embodiment, the gross morphology analyzer 132 analyzes the frequency content of the raw ECG signal across the n-second time period. For example, a low slope content may be determined. The low slope content may be approximated as the ratio of the number of slope data points less than a low slope threshold to the total number of data points determined during the n-second time period. Slope data points are determined as the sample-to-sample differences of the raw ECG signal. In one example, the low slope threshold may be defined as a percentage, for example 10%, of the largest absolute slope determined from the signal segment. The low slope content is then determined as the number of slope data points having an absolute value less than the low slope threshold to the total number of slope data points occurring in the n-second analysis time period.

The low slope content of non-shockable tachyarrhythmias is typically high relative to the low slope content of shockable tachyarrhythmias. As such, the low slope content is a useful ECG signal parameter to monitor for determining when a shock therapy is needed. As used herein, the term "shockable rhythm" refers to malignant or life threatening ventricular tachyarrhythmia, which can be terminated by shock delivery. "Non-shockable" refers to non-malignant heart rhythms that are not life threatening. In one embodiment, the low slope content is determined for at least two consecutive n-second time periods.

If the low slope content of two consecutive n-second time periods, or at least two of the most recent three n-second time periods is less than a detection threshold, and the single beat morphology analyzer 130 identified a predetermined minimum number of ventricular beats for the same n-second time periods, VF detector 118 generates a VF detection signal 146 provided to control module 110.

In other embodiments, frequency content of the n-second time periods may be evaluated by determining a relative high versus low frequency power, mean frequency or spectral width estimation, or probability density function to determine if the frequency content meets a VF detection criterion. One or more gross morphology metrics may be determined and compared to respective VF detection criteria. If gross morphology VF detection criteria and single beat morphology detection criteria (i.e. minimum number of beats identified as ventricular in origin) are both satisfied for a threshold number of consecutive n-second segments or some ratio of n-second segments, VF detection is made.

In alternative embodiments, VF detector 118 performs gross morphology analysis without relying on an R-wave sense signal 122. In this case, gross morphology analysis is performed as each n-second segment is acquired. Gross morphology metrics may be computed by analyzing the signal samples across the n-second segment and compared to VF detection criteria. If morphology matching metrics are desired for comparing the morphology of the signal within the n-second segment to a template, template matching on a shifted sample-by-sample basis could be performed. The number of times a template matches any segment of samples within the n-second segment would indicate a number of normal SVT beats within the n-second segment, for example. This template matching performed on a sample-by-sample basis can be performed instead of setting a morphology analysis window based on an R-wave sense signal. In this way, the VF detector 118 may operate independently of any R-wave sense signal 122 and be immune to oversensing or undersensing of the R-wave.

The morphology analysis performed by morphology analyzer 128 of SVT/VF/VF detector 116 may include the same or different morphology metrics as the morphology analysis performed by VF detector 118. VF detector 118 may receive the same raw ECG signal 124 as SVT/VT/VF detector 116 or a different ECG signal, e.g. from a different sensing vector and/or a different sensing channel having a different frequency bandwidth.

Cardiac signal analyzer 120 may include multiple SVT/VT/VF detectors 116 operating in parallel with multiple VF detectors 118 for each respective ECG signal being sensed when multiple sensing vectors and/or multiple sensing channels having different frequency bandwidths are being used to acquire ECG signals. Any one VF detector 118 may generate a VF detection signal 146 causing control module 110 to control signal generator 104 to deliver a shock pulse.

As shown in FIG. 4, each VF detector 118 can provide a single tachyarrhythmia detection signal corresponding only to VF. Each SVT/VT/VF detector 116 is enabled to provide multiple tachyarrhythmia detection signals (one at a time based on the current rhythm detection criteria being met), e.g. SVT 140, VT 142, or VF 144. A positive VF detection signal 146 from VF detector 118 takes priority in controlling therapy delivery over any output signal provided by SVT/VT/VF detector 116.

Figure 5:
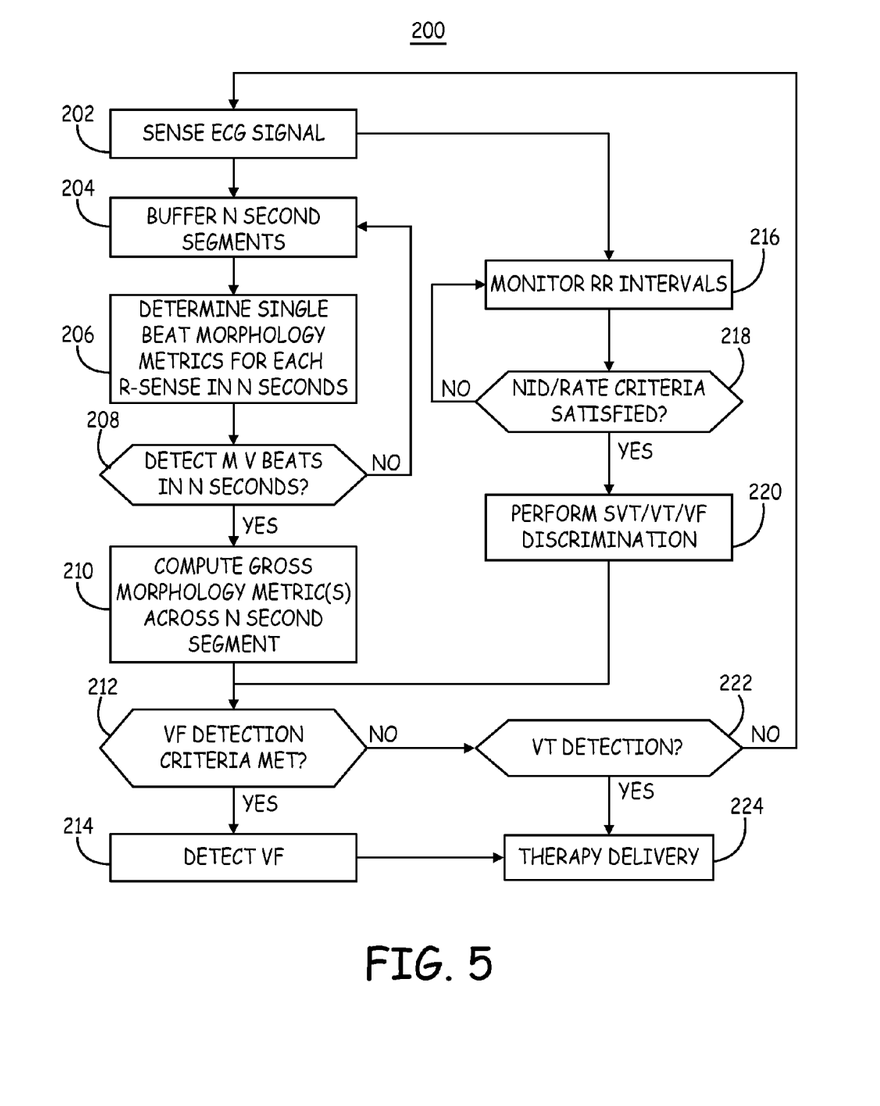
FIG. 5 is a flow chart of a method for detecting VF according to one embodiment.

FIG. 5 is a flow chart 200 of a method for detecting VF according to one embodiment. The method is implemented in an IMD including a VF detector as shown in FIG. 4 for detecting VF independent of RR interval counting or sorting in parallel to detection and discrimination of tachyarrhythmias using algorithms that involve RR interval counting or heart rate determination. At block 202, the ECG signal is sensed using one or more sensing vectors and one or more sensing channels which may have different pass band frequencies.

The raw ECG signal is buffered in a memory accessible by the VF detector in n-second segments at block 204. Single beat morphology metrics are determined for each R-wave sense event occurring during an n-second segment at block 206. A beat morphology analysis window may be established around the R-wave sense event, e.g. typically centered on the R-wave sense event. A morphology matching score and/or one or more beat features are determined for each R-wave sense event. Each event is classified as a normal, supraventricular beat; an abnormal, ventricular beat; or an unidentified beat. This beat classification operates continuously as n-second segments are buffered until a threshold number of ventricular beats are identified in an n-second segment.

If a threshold number of beats are classified as ventricular (V) beats during an n-second segment, as determined at block 208, gross morphology metrics are computed at block 210. The gross morphology metrics may be computed by analyzing the digitized sample points across the n-second segment without identifying individual beats or R-waves or setting any analysis window within the n-second segment. The gross morphology metrics are compared to VF detection criteria to determine if both the beat morphology VF detection criteria (i.e. a threshold number of ventricular beats) and the gross morphology detection criteria, e.g. a low slope content, are both met for the same n-second segment. If both criteria are met for a required number of n-second segments, VF detection criteria are satisfied at decision block 212. If the gross morphology criteria are not satisfied for an n-second segment identified to have a threshold number of ventricular beats, the VF detector operation may return to block 202 to continue monitoring the buffered n-second segments.

If VF detection criteria are met, VF is detected at block 214 and therapy is delivered at block 224. Accordingly, when three-second segments are buffered, VF detection may be made in as little as six seconds if two consecutive segments meet detection criteria, even in the presence of R-wave undersensing.

Simultaneously and in parallel to the VF detector operations performed at blocks 206 through 212, an SVT/VT/VF detector is monitoring RR intervals at block 216 to count intervals falling into a VT or VF interval range or sort RR intervals for determining a heart rate. If a VT or VF (or combined count) counter reaches a programmed NID, or a heart rate threshold is exceeded, as determined at block 218, SVT/VT/VF rhythm confirmation and discrimination is performed at block 220. Rhythm discrimination may involve single beat and/or gross morphology analysis or other morphology analysis to classify the tachyarrhythmia as SVT, VT or VF.

A corresponding output signal is provided to processing and control module 110. While not explicitly shown in FIG. 5, if a VF detection output signal is provided, control module 110 may respond immediately by advancing to therapy delivery block 224. Otherwise, before control module 110 makes a therapy decision based on a rhythm detection signal from the SVT/VT/VF detector, control module 110 checks if a VF detection signal is being received from VF detector (blocks 212, 214). If the VF detector 118 is not detecting VF, the control module 110 responds to the detection signal provided by SVT/VT/VF detector 116 at block 222. For example, if an SVT detection signal is being received from SVT/VT/VF detector 116, shock therapy is withheld as long as VF detector 118 is not providing a VF detection signal. If SVT/VT/VF detector 116 is detecting VT at block 222, control module 110 controls the signal generator 104 to deliver a programmed therapy at block 224, which may include anti-tachycardia pacing therapies, as long as the VF detector 118 is not generating a VF detection signal. If neither the VF detector 118 nor the SVT/VT/VF detector 116 is detecting a ventricular (VT or VF) rhythm, the process returns to block 202 and continues monitoring the ECG signal using the parallel detection methods.

Figure 6:
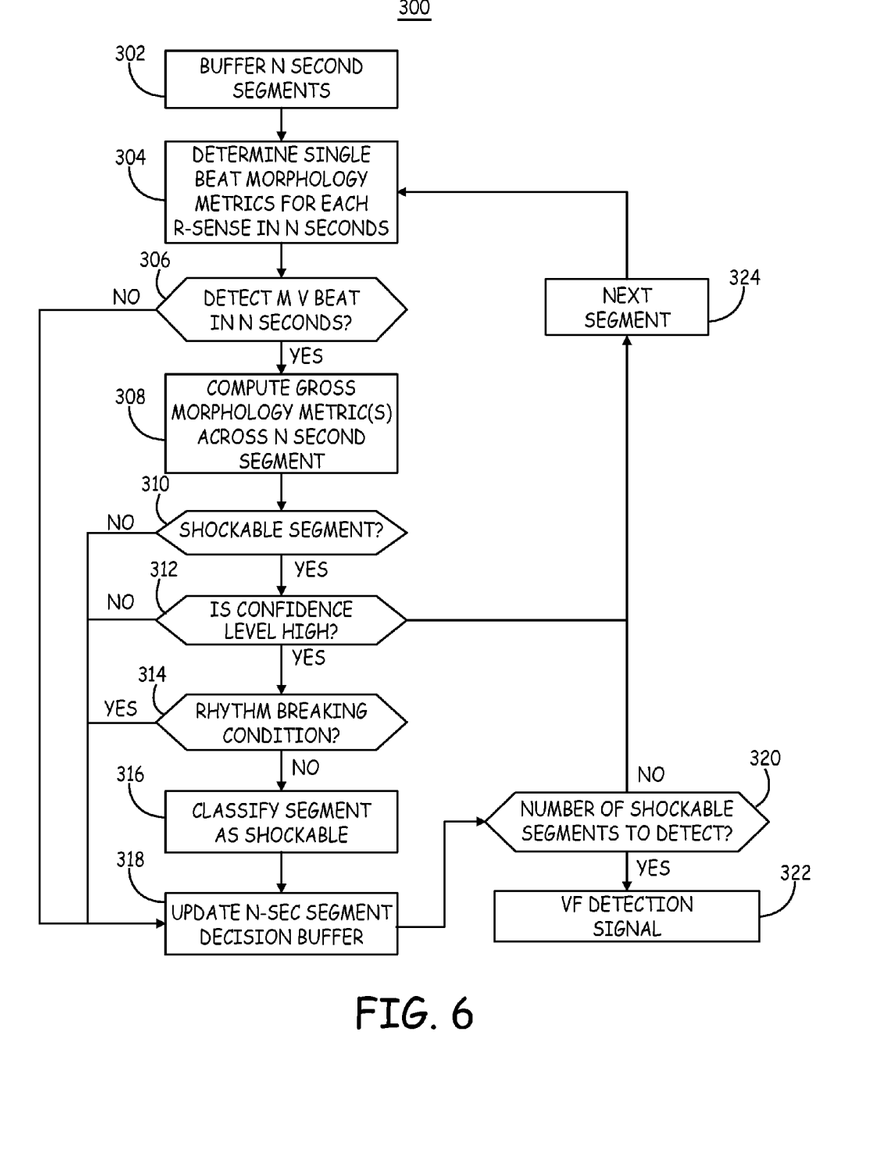
FIG. 6 is a flow chart of a method performed by a VF detector according to one embodiment.

FIG. 6 is a flow chart 300 of a method performed by a VF detector according to one embodiment. Initially, n-second ECG signal segments are buffered in a memory accessible by the VF detector at block 302. At block 304, single beat morphology metrics are determined for each beat corresponding to an R-wave sense signal during the n-second segment. Each beat is classified as a normal, supraventricular beat; abnormal, ventricular beat; or unidentified beat in response to the single beat metrics.

At block 306, the VF detector determines if a threshold number of ventricular beats are detected during the current n-second segment. If a threshold number of ventricular beats are not identified during the n-second segment, a segment decision buffer is updated at block 318 by clearing the oldest n-second segment decision from the buffer and storing the current n-second segment classification. A desired number of n-second segment decisions may be buffered on a first-in-first-out basis. The n-second segment decision buffer thus stores the classifications of the most recent n-second segments as being shockable rhythms or not shockable rhythms for use in making a VF detection decision. If the VF detector does not detect at least m ventricular beats in the n-second segment, the decision buffer is updated to store the current segment classification as "not shockable."

If a threshold number of ventricular beats are identified at block 306, for example if at least six ventricular beats are identified during a three-second segment, gross morphology metrics are computed for the n-second segment at block 308. The gross morphology metrics, such as a low slope content and a frequency content, are compared to VF detection thresholds. If VF detection thresholds are met based on the gross morphology metric(s), the segment is preliminarily classified as a shockable segment at decision block 310 based on the morphology analysis. If the segment is not classified as shockable based on gross morphology analysis, the n-second segment decision buffer is updated at block 318 to store the current segment classification as "not shockable." The process returns to block 304 to determine single beat metrics for the next n-second segment.

If the segment is classified as shockable at block 310 based on identifying m ventricular beats and based on the gross morphology metrics, the confidence of this classification is assessed at block 312. In one embodiment, an activity sensor signal input to VF detector 118 is checked at block 312. If an activity sensor signal is not below a threshold indicating a low level of activity, the confidence in the shockable classification of the segment is low; the segment is not classified or counted as a shockable segment. Additionally or alternatively, a noise analysis algorithm may report that the segment is noise contaminated. If noise contamination is present, the confidence in the shockable classification is low. If the confidence is low at block 312, the process updates the n-second segment decision buffer at block 318 to indicate the current segment is not a shockable segment, and the oldest segment classification stored in the buffer is cleared.

A high confidence in the shockable classification as determined at block 312, however, advances the process to block 314 where the VF detector checks whether a rhythm breaking condition is detected. A rhythm breaking condition is a condition that indicates that a break in a tachyarrhythmia rhythm may have occurred. A non-sustained tachyarrhythmia is not considered a shockable rhythm since it self-terminates. A rhythm breaking condition may be evidenced by at least two consecutive normal supraventricular beats. If two consecutive beats are identified as normal, supraventricular beats during the n-second segment, a rhythm break may have occurred. In some embodiments, detecting a rhythm breaking condition also includes detecting a long RR interval. However, since the VF detector 118 may operate without counting or measuring RR intervals, detection of a long RR interval may not be included in processes employed by VF detector 118 to detect a rhythm break. Criteria for detecting a rhythm breaking point may be based on morphology only in some embodiments. A segment containing a rhythm breaking condition is not classified or counted as a shockable segment. The process advances to block 318 to update the n-second segment decision buffer accordingly and returns to block 304.

If a rhythm breaking condition, e.g. two consecutive SVT beats, is not detected at block 314, the current n-second segment is classified as a shockable segment. The segment is classified as a shockable segment at block 316 when the single beat morphology analysis, the gross morphology analysis, and the confidence level all satisfy VF detection criteria and a rhythm breaking condition is not found during the n-second segment. It is recognized that the criteria applied to classify a segment as a shockable segment may be applied in a different order than the particular order shown in flow chart 300. For example, the activity sensor signal, noise analysis, and/or rhythm breaking conditions may be evaluated before performing gross morphology analysis.

If the segment is classified as a shockable segment at block 316, the n-second segment decision buffer is updated at block 318 by clearing the oldest segment classification and updating the most recent segment classification as "shockable." At decision block 320, the classifications of segments stored in the decision buffer are compared to a required number of shockable segments to detect VF. If the required number of shockable segments has not been reached, the process returns to block 324 to analyze the next n-second segment. A required number of segments classified as shockable segments (as stored in the decision buffer at block 318), for example two consecutive segments, may results in VF detection. In another example, if at least two out of the most recent three consecutive segments are classified as shockable segments, the required number of shockable segments to detect VF is satisfied. A VF detection signal is provided to the control module 110 at block 322.

Thus, a method and apparatus for performing tachyarrhythmia detection have been presented in the foregoing description with reference to specific embodiments. For example, various methods described herein may include steps performed in a different order or combination than the illustrative examples shown and described herein as long as a morphology-based VF detector is enabled to operate in parallel to a rate-based SVT/VT/VF detector to detect VF. It is appreciated that various modifications to the referenced embodiments may be made without departing from the scope of the disclosure as set forth in the following claims.

The invention claimed is:

1. A medical device for detecting and treating tachyarrhythmia, comprising:
   a plurality of electrodes to sense a cardiac signal;
   a sensing module coupled to the plurality of electrodes to sense cardiac events in response to the cardiac signal;
   a first processing module coupled to the sensing module and configured to:
   determine a first morphology metric for each sensed cardiac event occurring during a time segment of the cardiac signal;
   determine a count of the first morphology metrics corresponding to an event originating in a ventricular chamber;
   determine a second morphology metric for the time segment of the cardiac signal in response to the count of the first morphology metrics meeting a threshold number of events; and
   classify the time segment as a shockable segment in response to the second morphology metric meeting a detection criterion;
   the first processing module further configured to generate only a ventricular fibrillation detection signal in response to the time segment being classified as a shockable segment;

a second processing module configured to determine a number of tachyarrhythmia intervals between the sensed cardiac events in parallel to the first processing module computing of the first morphology metrics, the second processing module further configured to detect a tachyarrhythmia in response to determining the number of tachyarrhythmia intervals; and override the tachyarrhythmia detection when a shockable rhythm is detected by the first processing module in response to the number of time segments meeting the detection threshold.

2. The device of claim 1, wherein the second processing module is further configured to:

responsive to detecting a tachyarrhythmia, determine a third morphology metric in response to the sensed cardiac signal;

classify the tachyarrhythmia as one of a supraventricular tachyarrhythmia, ventricular tachyarrhythmia and ventricular fibrillation;

the control module further configured to respond to the classified tachyarrhythmia in the absence of the first processing module detecting a shockable rhythm in response to the number of time segments.

3. The device of claim 1, wherein determining the first morphology metric comprises setting a morphology window encompassing the sensed event and determining during the window at least one of a sensed event width, a sensed event amplitude, and a similarity to a morphology template.

4. The device of claim 1, wherein determining the second morphology metric comprises determining across the time segment at least one of a low slope content and a frequency content.

5. The device of claim 1, wherein the first processing module is configured to provide only a single tachyarrhythmia detection output signal corresponding only to ventricular fibrillation in response to detecting the shockable rhythm, and wherein the second processing module is configured to provide multiple tachyarrhythmia detection signals selected one at a time from a supraventricular tachycardia output signal, a ventricular tachycardia output signal and a ventricular fibrillation output signal based on the determined number of tachyarrhythmia intervals and the outcome of the third morphology analysis.

6. The device of claim 1, wherein the first processing module is further configured to:

determine a number of time segments classified as a shockable segment; and detect a shockable rhythm in response to the number of time segments meeting a detection threshold.

7. The device of claim 6, further comprising:

an activity sensor for sensing an activity signal; and the first processing module coupled to the activity sensor and further configured to, in response to detecting an activity signal above a low activity threshold, inhibit the counting of the time segment as a shockable segment.

8. The device of claim 6, wherein the first processing module is further configured to:

detect a rhythm breaking condition during the time segment; and responsive to detecting the rhythm breaking condition, inhibit counting the time segment as a shockable segment.

9. The device of claim 6, further comprising a signal generator coupled to the electrodes; and a control module coupled to the first processing module and the signal generator and configured to control the signal generator to deliver a defibrillation shock in response to the first processing module detecting the shockable rhythm.

10. A non-transitory, computer-readable medium storing a set of instructions, which when executed by a processor of a medical device causes the device to:

determining a cardiac signal using a plurality of electrodes coupled to a sensing module;

determine cardiac events in response to the cardiac signal;

determine a first morphology metric for each sensed cardiac event occurring during a time segment of the cardiac signal;

determine a count of the first morphology metrics corresponding to an event originating in a ventricular chamber;

determine a second morphology metric for the time segment of the cardiac signal in response to the count of the first morphology metrics meeting a threshold number of events; and classify the time segment as a shockable segment in response to the second morphology metric meeting a detection criterion; and generate only a ventricular fibrillation detection signal in response to the time segment being classified as a shockable segment determine a number of tachyarrhythmia intervals between the sensed cardiac events in parallel to the computing of the first morphology metrics, detect a tachyarrhythmia in response to determining the number of tachyarrhythmia intervals; and override the tachyarrhythmia detection when a shockable rhythm is detected by the first processing module in response to the number of time segments meeting the detection threshold.

11. A medical device, comprising:

a plurality of electrodes;

a sensing module coupled to the plurality of electrodes for sensing a cardiac signal;

a therapy delivery module coupled to the plurality of electrode for delivering a therapy;

a first processing module coupled to the sensing module and configured to:

determine a first morphology metric for each individual one of a plurality of cardiac events occurring during a time segment of the cardiac signal, classify each individual one of the plurality of cardiac events as at least one of a supraventricular beat and a ventricular beat by comparing each of the first morphology metrics to beat classification criteria, responsive to a minimum number of the individual ones of the plurality of cardiac events being classified as ventricular beats, determining a second morphology metric by analyzing signal samples across the n-second segment independent of identifying the cardiac events, classify the time segment as a shockable segment in response to the second morphology metric meeting a detection criterion, and generate an output signal in response to the time segment being classified as a shockable segment wherein the output signal is only a ventricular fibrillation detection output signal; and a second processing module coupled to the sensing module and configured to:

determine intervals between cardiac events of the cardiac signal in parallel to the first processing module determining the first morphology metrics, determine a count of the determined intervals meeting tachyarrhythmia criteria, in response to the count meeting ventricular tachycardia criteria determining a third morphology metric of the cardiac signal, and generate an output signal selected from a supraventricular tachycardia output signal, a ventricular tachycardia output signal, and a ventricular fibrillation output signal in response to the count meeting the tachyarrhythmia criteria and in response to the morphology metric if it is determined; and a control module configured to receive the first processing module output signal and the second processing module output signal and make a therapy decision for controlling the therapy delivery module based on the first processing module output signal and the second processing output signal.

* * * * *